United States Patent [19]

Thompson

[11] Patent Number: 4,961,739

[45] Date of Patent: Oct. 9, 1990

[54] WAVEFORM GENERATOR FOR ELECTROSURGICAL APPARATUS

[75] Inventor: Richard K. Thompson, Aurora, Colo.

[73] Assignee: Aspen Labatories, Inc., Greenwood Village, Colo.

[21] Appl. No.: 165,143

[22] Filed: Mar. 7, 1988

[51] Int. Cl.$^5$ ............................................. A61B 17/39
[52] U.S. Cl. ..................................... 606/37; 606/39; 606/40
[58] Field of Search ...................... 128/303.13, 303.14, 128/303.17; 606/37–40

[56] References Cited

U.S. PATENT DOCUMENTS 4,617,927 10/1986 Manes ............................. 128/303.14
4,658,820 4/1987 Klicek .

Primary Examiner—Lee S. Cohen
Assistant Examiner—David Shay
Attorney, Agent, or Firm—Fields, Lewis, Pittenger & Rost

[57] ABSTRACT

A waveform generator for electrosurgical apparatus disclosed includes a MxNxP storage device and a parallel to series conversion device. For the storage device, M is the maximum number of different waveforms being stored, N equals the number of bits being output from the storage device at a time and P is the maximum number of N bits that can be stored for each waveform. An address counter selects the next N bits of the waveform and these N bits loaded from the storage device into the conversion device and output in a sequential or series output signal to drive the RF power amplifier of electrosurgical apparatus. The output signal has a bit rate N times faster than the storage device is accessed.

7 Claims, 3 Drawing Sheets

WAVEFORM GENERATOR FOR ELECTROSURGICAL APPARATUS

TECHNICAL FIELD

This invention relates generally to improvements in electrosurgical apparatus and more particularly to a novel and improved waveform generator for controlling the power output of electrosurgical apparatus.

BACKGROUND ART

Electrosurgical apparatus for cutting and the coagulation of tissue requires supplying a wide range of power outputs to the active electrode for a wide range of surgical procedures.

Klicek U.S. Pat. No. 4,658,820 discloses a waveform generator that stores several waveforms in an MxN storage device, each of these several waveforms being available simultaneously at the output of the storage device and with the desired waveform selected by a multiplexer. That disclosure requires that the read access time of the storage device be less than the highest bit rate of the resulting waveform, that each waveform length must be of a common multiple of every other waveform length, and that the number of waveforms that can be stored is limited by the length of the multiplexer used to select the output waveform. Those requirements place severe restrictions on the upper waveform frequency, diversity of waveform length, and the number of waveforms that may be used.

DISCLOSURE OF INVENTION

The waveform generator disclosed includes a MxNxP waveform storage device, a parallel to serial conversion means loaded by the storage device for changing this stored waveform to a sequential or series output signal, and a means of controlling these operations. The sequential or series output signal drives the RF power amplifier connected to the active electrode of the electrosurgical apparatus. Control means, preferably an address counter that selects each N bits of the waveform from the storage device has a selectable modulus without external decoding circuitry.

DETAILED DESCRIPTION

Figure 1:
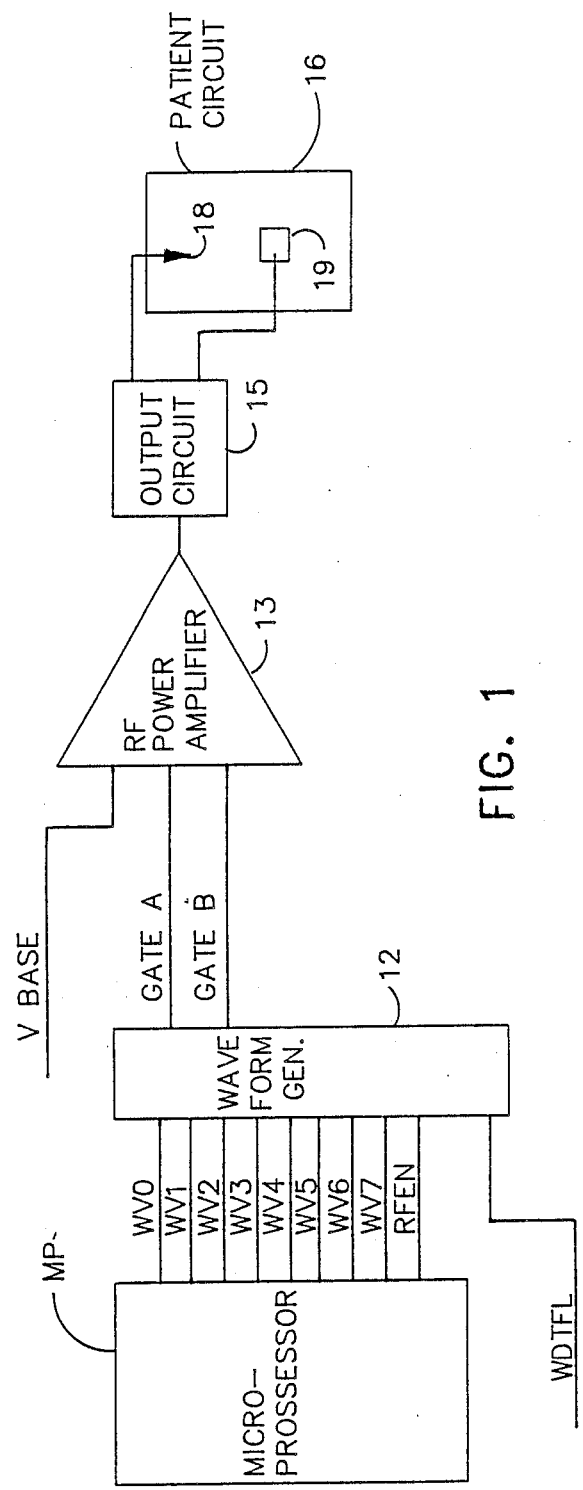
FIG. 1 is a schematic diagram of the waveform generator embodying features of the present invention associated with other parts of the electrosurgical apparatus.

Referring now to FIG. 1 there is shown a waveform generator 12 having eight select address input lines WVØ-WV7 and RFEN input lines receiving outputs from a controller MP, preferably a programmed microprocessor. An additional input line WDTFL receives its signal from a watchdog timer circuit (not shown). The RFEN line carries an RF enable signal supplied by the controller MP that will turn off the gates of the buffer U7A and U7B as required. The WDTFL line carries a watchdog timer fail signal supplied by a watchdog timer that will turn off the buffers if the microprocessor is not working properly. The waveform generator 12 shown has two outputs GATE A and GATE B which are applied to the input of a RF power amplifier 13 of the electrosurgical apparatus. An output circuit 15 couples the output of the RF power amplifier to a patient circuit 16 which includes an active electrode 18 and the return electrode 19. A VBASE signal from a digital to analog converter (not shown) is also applied as an input to the RF power amplifier to control the amplitude of the waveform generated by generator 12.

Figure 2A:
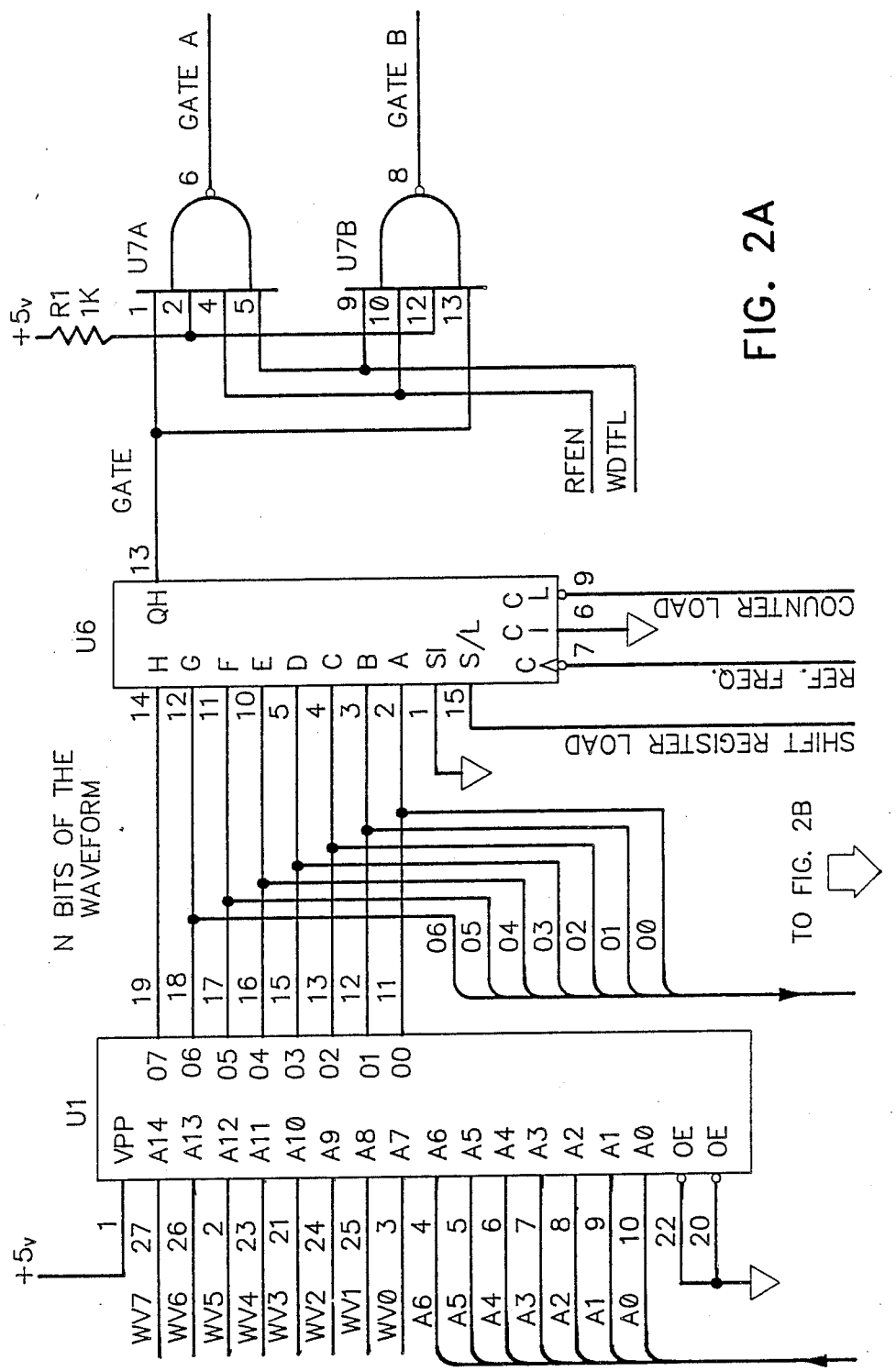
FIG. 2A is a portion of a more detailed circuit diagram of a waveform generator shown in block form in FIG. 1.
Figure 2B:
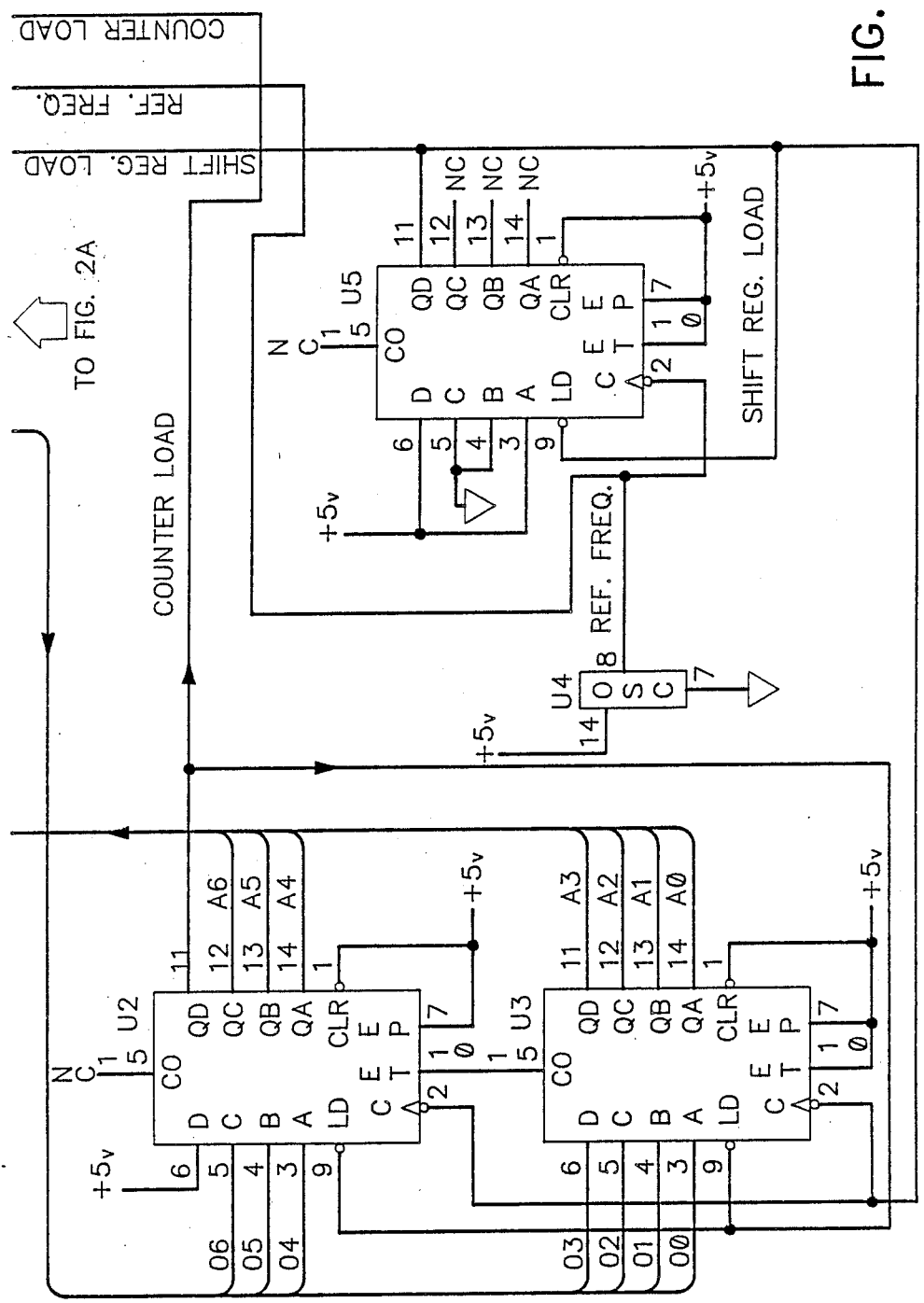
FIG. 2B is the remainder of the more detailed circuit diagram of a waveform generator shown in block form in FIG. 1.

Referring now to FIGS. 2A and 2B, a MxNxP storage device U1 is provided. The storage device shown is an EPROM. M is the maximum number of different waveforms that can be stored. P is the maximum number of N bits stored for each waveform. N is the number of bits being output from the storage device at a time. NxP is the maximum length of each waveform in number of bits outputted. The read access time of the storage device is less than N times the output bit stream. The waveform is selected through microprocessor control of the eight address lines WVØ-WV7.

An address counter made up of U2 and U3 provides a COUNTER LOAD signal to set the modulus of the counter, and SUBADDRESS lines AØ-A6 to select the next N bits of the waveform. An N bit signal will be output from storage device U1 and loaded into a parallel-to-serial conversion device U6 preferably a parallel-in, series-out shift register. The shift register U6 converts the N bits to a sequential or serial output that is buffered by buffers U7A and U7B to provide the GATE A and GATE B outputs. The GATE A and GATE B outputs are two identical outputs both of which are used to drive one half of the RF POWER AMPLIFIER 13. This split drive allows the power amplifier to be partially functional even if one half of the power amplifier fails.

A clock oscillator U4 generates a REFERENCE FREQUENCY signal which in a preferred embodiment is 20MHz. Each serial output bit preferably has a duration of 50 nanoseconds. The buffers U7A and U7B provide both buffer and enable functions.

A counter U5 is configured as a divide by N (N=8 in this embodiment) and has a QD output set high when it is loaded with the preset values. As the count increases from it's preload value to a 1111 output and then rolls over to a ØØØØ output, QD goes low, loads shift register U6 with the outputs (OØ-07) of storage device U1, and synchronously loads counter U5 to it's preload state of 1ØØ1. Shift register U6 then synchronously and sequentially shifts those outputs through its own output labeled GATE at the REFERENCE FREQUENCY rate. This is the unbuffered drive signal for the power amplifier.

With reference to address counter U2,U3, the most significant bit MSB which is QD of U2 is set high by the preload. This sets the load inputs/LD of U2 and U3 to their inactive state and allows the address counter to count. This counter keeps counting until full value 1111 1111 and then rolls over to ØØØØ ØØØØ, setting QD of U2 low and thus COUNTER LOAD low. On the next clock from SHIFT REGISTER LOAD there is loaded all of the inputs 0Ø through 06 into the address counter U2, U3. This is to be distinguished from starting the counter at ØØØØ and decoding an output to reset. This feature gives a parts count advantage by eliminating a separate decoding device and also allows the use of a faster clock for the counter by eliminating the delay time associated with a separate decoding device.

Each time counter U5 cycles through it's count, the SHIFT REGISTER LOAD signal goes low and then high to advance the count of the address counter U2, U3. The outputs from the address counter A0-A7 select the next N bit word to be loaded into shift register U6 from storage device U1. When the address counter U2, U3 reaches its full count i.e. the entire waveform has been completely outputted, the COUNTER LOAD signal goes low on the next count and the address counter U2, U3 is preloaded to the pattern presented to it by O0-07 of storage device U1. This pattern sets the modulus of the address counter and the COUNTER LOAD signal also clears the shift register U6 to zero's to prevent putting the modulus pattern out to the RF power amplifier.

The waveform generator 12 discussed herein stores the waveform to be output and can store several waveforms of unrelated frequency and bit patterns limited only by the clock oscillator U4 and the size of the storage device U1. The shift register U6 is loaded with data from the storage device U1 to allow a more complex bit pattern to be generated. The pulse is characterized by its pulse width or duration, and pulse repetition frequency or repetition rate. The minimum pulse width for the preferred embodiment is 50 nanoseconds.

A wide variety of waveforms are possible from the waveform generator of the present invention to carry out a wide variety of surgical procedures. For example, for a bipolar coagulation mode the RF frequency is 1.05 Mhz. The number of pulses that occur is controlled by the power setting on the front panel. The first waveform has no pulse and each consecutive waveform has an additional pulse with a selected time interval between pulses over the previous waveform. The unit is calibrated such that each pulse corresponds to one watt delivered to the rated load impedance. The maximum power setting for the bipolar coag made is 50 watts, thus the maximum number of pulses per waveform cycle is 50, and the number of required waveforms for this is 51. The advantages of this kind of waveform and control scheme are that power output is controlled by selecting a waveform, making it very predictable, and peak output voltage does not increase with increased power settings (due to fixed control voltage and amplifier ON time). This provides a well controlled "cook" of the tissue and practically eliminates tissue popping at higher power levels.

A bipolar cut mode operates at 1.00 Mhz and is controlled by the VBASE voltage that is supplied to the RF power amplifier 13. The purpose of a cut mode is to cut tissue with as little hemostasis as possible. This is done by supplying as much power with as little voltage and muscle stimulation as possible. The RF frequency for the monopolar cut is 416.7 Khz. This waveform makes use of the variable modulus for the waveform cycle.

The monopolar blend mode provides cutting action with hemostasis. This is done by increasing the crest factor. Crest factor is equal to peak voltage divided by r.m.s. voltage. To do this, a normal cut waveform is used, but only at a partial duty cycle. This then requires a higher voltage to be used to deliver the required power, thus causing the desired hemostasis.

A standard coagulation mode is used when hemostasis without a cutting action is desired. This mode has a higher crest factor than the monopolar blend (about 6 vs. 3 for blend and 1.7 for cut). Power is controlled by a waveform selection. There are two pulses per waveform cycle and the length of each pulse increases with power setting. The length and PRF (pulse repetition frequency) of these pulses determines output voltage and power. With this waveform, first one pulse increases, then the other on the ensuing waveform when power is increased. This provides for a fine control of waveform power.

A monopolar spray mode is used when even more peak voltage is required than monopolar standard coag. This would be used for a very bloody operating field such as the sternum. This mode has a crest factor of about 9. In order to generate the higher voltage without increasing the power delivery, the number of pulses per waveform cycle is half that of monopolar standard coag mode. Like monopolar standard coag and bipolar coag, output power is determined by waveform selection.

By way of illustration only and not by limitation, there are listed below devices that have been found suitable for use in the illustrated circuits:

| Reference No. | Part No. | Manufacturer |
| --- | --- | --- |
| U1 | 27256 | INTEL |
| U2, U3, U5 | 74LS163 | TEX. INSTR. |
| U4 | RASC0-1 | MOTOROLA |
| U6 | 74LS166 | TEX. INSTR. |
| U7A, U7B | 74S140 | TEX. INSTR. |
| MP | 8031 | INTEL |

It is understood that a number of variations are possible with the above described apparatus. For example, the storage device U1 could be a RAM that is loaded by a microprocessor. The microprocessor could calculate the desired waveform to be stored in the RAM. A ROM or PROM could also be used. The counter preloads for the address counter U2,U3 could be fixed, with the stored waveform modified to accommodate this change. This would eliminate the requirement to clear the shift register when loading the modulus preload. The address counter preload could come from an independent source, i.e. a latched microprocessor input, or another storage device that uses the same waveform address lines as the waveform storage device, but contains only modulus lengths. This would also eliminate the requirement to clear the shift register when loading the modulus preload. The shift register U6 could be any parallel to serial conversion device such as a multiplexer with a counter. The clock oscillator U4 could be a different frequency, and could be controlled to offer variations of output frequency without adding to the size of the memory. The length of the parallel to serial converter could be different. This same length would be required for the modulus of the counter U5. The address counter U2, U3 could be a different length to accommodate a different waveform modulus or to use less memory when used only for shorter modulus waveforms.

From the foregoing, the advantages of the waveform generator of the present invention include a longer, more complex bit pattern and a variable length count. The preferred embodiment uses approximately 200 different waveforms and could store 256 different, independent waveforms. The modulus of the waveform is stored in the storage device so that the modulus can be set for each waveform without external intervention. The waveform generator of the present invention allows the use of a slower MxNxP memory device. The address counter modulus is set by preloading the value P−K/N into the waveform address counter and resetting when the count rolls over. K is the total number of bits output for each waveform.

Although the present invention has been described with a certain degree of particularity, it is understood that the present disclosure has been made by way of example and that changes in details of structure may be made without departing from the spirit thereof.

What is claimed is:

1. A waveform generator for controlling the waveform and power output of electrosurgical apparatus, said waveform generator comprising:

a clock for providing a REFERENCE FREQUENCY signal, a counter responsive to said REFERENCE FREQUENCY signal that counts to a selected number and then provides a SHIFT REGISTER LOAD signal, an address counter responsive to a N BITS OF THE WAVEFORM signal and to said SHIFT REGISTER LOAD signal, said address counter providing a COUNTER LOAD signal and a SUBADDRESS signal for selecting each N bit word, an MxNxP storage means for storing waveforms where M is the maximum number of a plurality of different waveforms being stored, each waveform having a maximum length of N times P, N equals the number of a plurality of bits being output in parallel from the storage means at a time and P is the maximum number of a plurality of N bits stored for each waveform, said storage means having input address lines for selecting each waveform and a plurality of parallel output lines for providing a N bits of the waveform at a time, and said address counter having a counter modulus, said counter modulus being set by preloading a selected count from said storage means which selected count provides a waveform of a selected repetition frequency over a range of frequencies, reading a full count and counting to zero, as upper bit of said address counter going to zero and reloading the preloaded count, a parallel to serial shift register loaded by the N bits of the waveform in response to said SHIFT REGISTER LOAD signal, said COUNTER LOAD signal, and said REFERENCE FREQUENCY signal for converting the N bits of the waveform to a SINGLE BIT SERIAL WAVEFORM output signal for controlling power output, said output signal being selected by said SUBADDRESS signal at a speed determined by said REFERENCE FREQUENCY signal, said output signal having a maximum bit output time N times faster than the read access time of said storage means.

2. A waveform generator as set forth in claim 1 wherein said REFERENCE FREQUENCY signal is 20MHz and each bit is 50 nanoseconds in duration.

3. A waveform generator as set forth in claim 1, wherein the shift register is loaded N bits at a time and shifted out one bit at a time.

4. A waveform generator as set forth in claim 1 wherein there are eight parallel lines into said shift register.

5. A waveform generator as set forth in claim 1 wherein there are eight address lines into said storage means.

6. A waveform generator as set forth in claim 1 wherein said output signal from said shift register is applied to a buffer before being coupled to a RF power amplifier of the electrosurgical apparatus.

7. A waveform generator as set forth in claim 6 wherein N equals eight.

* * * * *